United States Patent [19]

Mehrotra

[11] Patent Number: 5,047,511

[45] Date of Patent: Sep. 10, 1991

[54] METHOD FOR RECOVERING RECOMBINANT PROTEINS

[75] Inventor: Vikram P. Mehrotra, Terre Haute, Ind.

[73] Assignee: Pitman-Moore, Inc., Lake Forest, Ill.

[21] Appl. No.: 399,021

[22] Filed: Aug. 28, 1989

[51] Int. Cl.$^5$ .................... C07K 15/14; C07K 15/06; C07K 3/24

[52] U.S. Cl. .................... 530/399; 530/350; 530/419; 530/421; 435/69.4; 435/69.1

[58] Field of Search ............... 530/399, 350, 419, 421; 435/68, 69.4, 69.1

[56] References Cited

U.S. PATENT DOCUMENTS

| | | | |
|---|---|---|---|
| 2,175,090 | 10/1939 | Parfentjev | 167/78 |
| 3,252,961 | 5/1966 | Rodgers et al. | 260/112 |
| 3,657,071 | 4/1972 | Bergmeyer | 195/69 R |
| 3,749,668 | 7/1973 | Walker | 210/37 |
| 3,794,562 | 2/1974 | Bergmeyer et al. | 435/190 |
| 4,055,469 | 10/1977 | Snoke et al. | 195/66 R |
| 4,204,989 | 5/1980 | McAleer | 530/427 |
| 4,271,028 | 6/1981 | Marfurt et al. | 210/727 |
| 4,309,339 | 1/1982 | Haupt et al. | 530/395 |
| 4,325,866 | 4/1982 | Bohn | 530/395 |
| 4,634,673 | 1/1987 | Johnson et al. | 435/234 |
| 4,677,196 | 6/1987 | Rausch | 530/412 |
| 4,687,742 | 8/1987 | Skoet et al. | 435/234 |
| 4,693,828 | 9/1987 | Yoshioka et al. | 210/679 |
| 4,740,304 | 4/1988 | Tjerneld et al. | 210/639 |
| 4,761,472 | 8/1988 | Schultze | 540/145 |
| 4,771,104 | 9/1988 | Kodama et al. | 525/54.1 |
| 4,771,128 | 9/1988 | Ferris et al. | 530/417 |

OTHER PUBLICATIONS

*Kirk-Othmer Encyclopedia of Chemical Technology*, vol. 19, p. 531.

Primary Examiner—Margaret Moskowitz
Assistant Examiner—Keith C. Furman
Attorney, Agent, or Firm—Wendell R. Guffey; Thomas L. Farquer

[57] ABSTRACT

A method for recovering a recombinant protein from a protein solution containing high molecular weight contaminating proteins by directly adding a flocculant to the solution in amounts sufficient to selectively precipitate the high molecular weight protein contaminants is disclosed.

The high molecular weight precipitates are removed and the solution is further processed to remove low molecular weight contaminating proteins and other non-protein contaminants. The recombinant protein is subsequently recovered and further processed to produce a protein composition suitable for its intended use.

14 Claims, 1 Drawing Sheet

GPC Patterns of the Feed of the Precipitation Process with Superfloc 340.

GPC Patterns of the Feed of the Precipitation Process with Superfloc 340.

GPC Patterns of the Product of the Precipitation Process with Superfloc 340.

Product Recovery:
87.5% P/M <0.1

METHOD FOR RECOVERING RECOMBINANT PROTEINS

This invention relates generally to methods for recovering recombinant proteins and particularly to a method for recovering recombinant proteins from protein solutions containing high molecular weight contaminating proteins.

BACKGROUND OF THE INVENTION

Methods for producing recombinant proteins are well known in the art; heterologous DNA segments that encode for a particular protein are inserted into host microorganisms using recombinant DNA technology. By growing the transformant microorganisms under conditions which induce the expression of proteins, heterologous proteins such as insulin, somatotropins, interleukins, interferons, somatomedins, and the like can be produced.

Unfortunately, heterologous proteins produced by transformant microorganisms are frequently not biologically active because they do not fold into the proper tertiary structure when transcribed within the microorganism. The heterologous proteins tend to form aggregates which are recognizable within the cell as "inclusion bodies". These inclusion bodies may also be caused by the formation of covalent intermolecular disulfide bonds which link together several protein molecules to form insoluble complexes. The inclusion bodies generally contain mostly heterologous proteins and a small fraction of contaminating host microorganism proteins.

Several processes have been developed to extract the inclusion bodies from the microorganisms and convert the heterologous proteins contained therein into proteins having native bioactivity consistent with the natural parent or non-recombinant proteins. These processes generally involve disrupting the microorganism cell, separating the inclusion bodies from cell debris, solubilizing the inclusion body proteins in a denaturant/detergent which unfolds the protein, separating the heterologous inclusion body proteins from insoluble contaminants, removing the denaturant/detergent thereby allowing the heterologous proteins to refold into a bioactive tertiary conformation, and separating the protein from the contaminating proteins that remain in solution.

Several recombinant protein purification schemes following this general procedure are known in the art: U.S. Pat. Nos. 4,511,503 and 4,518,526 to Olson et al. and U.S. Pat. Nos. 4,511,502 and 4,620,948 to Builder et al. disclose multi-step methods wherein (1) inclusion bodies are solubilized in a strong denaturant and a reducing agent, (2) insoluble contaminants are removed from the solubilized protein solution, (3) the strong denaturant is replaced with a weak denaturant, (4) the protein is allowed to refold assisted by oxidation of the sulfhydryl groups to disulfide bonds using molecular oxygen and a catalyst, typically metal cations or sodium tetrathionate, and (5) the protein is separated from other contaminating proteins by membrane separation techniques or chromatography procedures.

Rausch et al., U.S. Pat. No. 4,677,196, incorporated herein by reference, discloses a particular method for purifying and activating proteins which is a variation of the general scheme described above. The method comprises solubilizing the inclusion bodies in SDS, removing the excess SDS from the solution using dialysis or other suitable technique, chromatographing the SDS-protein solution on an ion-retardation resin, and chromatographing the resulting solution on an anion-exchange resin to recover the protein.

All these known procedures share a common problem. The protein solution produced when the denaturant/detergent is removed contains the recombinant protein, low molecular weight contaminating proteins, non-protein contaminants, and high molecular weight contaminating proteins; the high molecular weight protein contaminants are often mostly dimers, oligomers and aggregates of the recombinant protein but also include non-recombinant proteins from the cell digest. It is often difficult, time consuming, and expensive to separate the recombinant protein from these contaminants, particularly the recombinant protein dimers, oligomers and aggregates. Chromatographic and membrane separation techniques may be effective for separating the recombinant proteins from the contaminants but are cumbersome, lengthy, expensive and often give low percentage yields for protein recovery.

Ho, U.S. Pat. No. 4,645,829, discloses a method for separating polypeptides by adding a charged polymer to the solution, preferably in the presence of a neutral polymer. The charged polymer is typically DEAE-Dextran (MW ~500,000 daltons) or SANTOFLOC (MW about 100,000 daltons). Similarly, low molecular weight flocculants have been used to separate proteinaceous materials from aqueous solution in several references, e.g., U.S. Pat. Nos. 3,313,795, 3,719,655, 4,766,224, and 4,726,947.

New and improved methods for easily, quickly, and inexpensively recovering high yields of recombinant proteins from solutions containing high molecular weight protein contaminants are therefore needed.

SUMMARY OF THE INVENTION

Figure 1:
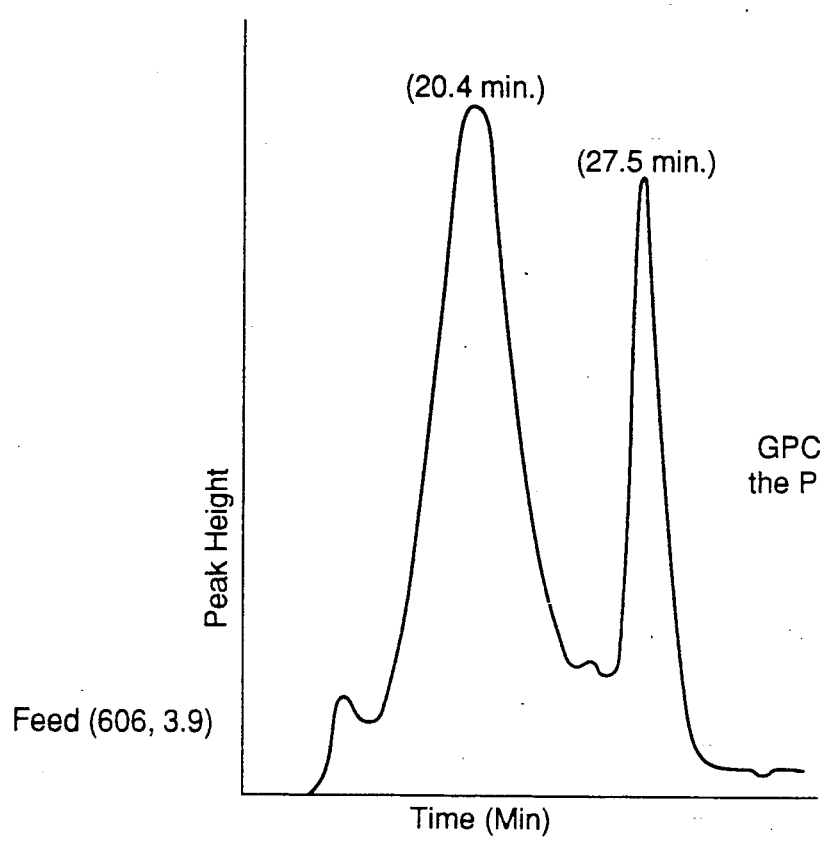
FIGS. 1 and 2 are graphic representation showing the Gel Permeation Chromatography (GPC) patterns of the feed and product using the present method with SUPERFLOC 340 flocculant.
Figure 2:
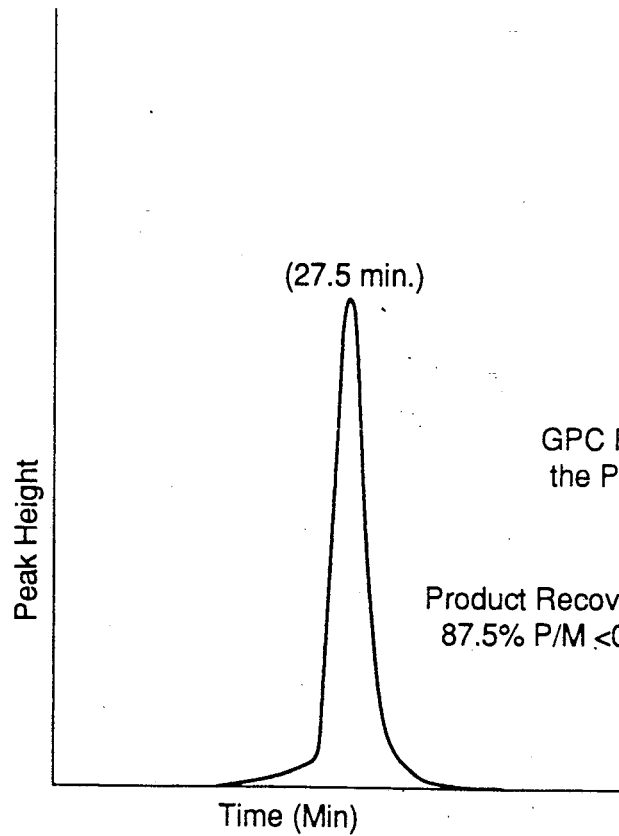

It is, therefore, an object of the present invention to provide a new method for easily, quickly, and inexpensively recovering high yields of recombinant proteins from protein solutions containing high molecular weight contaminating proteins.

It is another object of the present invention to provide a method for removing high molecular weight contaminating proteins from a recombinant protein solution thereby allowing the easy, quick, and inexpensive recovery of the recombinant protein.

These and other objects are achieved by directly adding a flocculant having a molecular weight of from about 100,000 to 12 million daltons to solutions containing high molecular weight contaminating proteins and a recombinant protein in amounts sufficient to selectively precipitate the high molecular weight protein contaminants. The flocculant induces preferential precipitation of proteins having a molecular weight greater than about 1.5 times the molecular weight of the recombinant protein, particularly recombinant protein dimers, oligomers and aggregates having a molecular weight greater than about 1.5 times the molecular weight of the recombinant protein. The precipitates are separated from the solution leaving the recombinant protein, low molecular weight contaminating proteins and other non-protein contaminants in solution. The recombinant protein is recovered from the solution using known techniques and processed to produce the desired protein product.

In the preferred embodiment, a cationic flocculant containing quaternary ammonium groups is added directly to the solution in amounts sufficient to produce a 0.005-1% solution by volume. The high molecular weight contaminating proteins precipitate and are removed from the solution by conventional means such as filtration, centrifugation, and the like. The resulting protein solution containing the recombinant protein, low molecular weight contaminating proteins and other non-protein contaminants is further processed using conventional techniques such as chromatography to recover the recombinant protein.

Other objects, advantages, and novel features of the present invention will become apparent from the following detailed description of the invention.

DETAILED DESCRIPTION OF THE INVENTION

The term "recombinant protein" as used herein defines a protein which one desires to recover in a relatively pure form and includes proteins having the amino acid sequence of native proteins and their analogs and muteins having substituted, deleted, replaced, or otherwise modified sequences.

The term "recombinant somatotropin" (rST) as used herein includes recombinant proteins having the amino acid sequence of native somatotropin, amino acid sequences substantially similar thereto, or an abbreviated sequence form thereof, and their analogs and muteins having substituted, deleted, replaced, or otherwise modified sequences. In particular, rST as used herein includes a protein of the same sequence as pST, but having amino acids deleted from its amino terminal end. Examples of such proteins include but are not limited to delta-7 recombinant porcine somatotropin, delta-4 recombinant bovine somatotropin, and the like.

The term "high molecular weight contaminating proteins" or "high molecular weight protein contaminants" as used herein refers to proteins having a molecular weight greater than about 1.5 times the molecular weight of the recombinant protein, particularly recombinant protein dimers, oligomers and aggregates having a molecular weight greater than about 2 times the molecular weight of the recombinant protein.

The term "low molecular weight contaminating proteins" or "low molecular weight protein contaminants" as used herein refers to proteins having a molecular weight less than about 1.5 times the molecular weight of the recombinant protein.

The term "non-protein contaminants" as used herein refers to relatively low molecular weight substances such as precipitating agents, solubilizing agents, oxidizing agents, reducing agents, and the like, which are typically in a protein solution.

According to the present invention, a method is provided for recovering a recombinant protein from a protein solution containing high molecular weight contaminating proteins. The method comprises directly adding a flocculant having a molecular weight of from about 100,000 to 12 million daltons to the solution containing high molecular weight contaminating proteins and the recombinant protein in amounts sufficient to selectively precipitate the high molecular weight protein contaminants. The flocculant preferentially induces the precipitation of proteins having a molecular weight greater than about 1.5 times the molecular weight of the recombinant protein, particularly recombinant protein dimers, oligomers and aggregates having a molecular weight greater than about 2 times the molecular weight of the recombinant protein. The method provides an improved method for easily, quickly, and inexpensively recovering high yields of recombinant proteins from solutions containing high molecular weight protein contaminants.

In the preferred embodiment, a cationic flocculant containing quaternary ammonium groups is added directly to the solution in amounts sufficient to produce a 0.005-1% solution by volume. The high molecular weight contaminating proteins precipitate and are removed from the solution by conventional means such as filtration, centrifugation, and the like. The resulting protein solution containing the recombinant protein, low molecular weight contaminating proteins and other non-protein contaminants is further processed using conventional techniques such as chromatography to recover the recombinant protein.

In the most preferred embodiment, a method is provided for recovering recombinant somatotropins (molecular weight about 20,000) by directly adding a cationic flocculant containing quaternary ammonium groups to a solution containing high molecular weight contaminating proteins and recombinant somatotropins in amounts sufficient to selectively precipitate the high molecular weight protein contaminants. The cationic flocculants preferentially induce the precipitation of proteins having a molecular weight greater than about 1.5 times the molecular weight of the recombinant somatotropin (molecular weight greater than about 30,000), particularly recombinant somatotropin dimers, oligomers and aggregates having a molecular weight greater than about 2 times the molecular weight of the recombinant somatotropin (molecular weight about 40,000 and up). The present method, therefore, provides a method for separating the recombinant somatotropin from its bioinactive dimers, oligomers and aggregates.

Solutions containing a recombinant protein, non-protein contaminants, high molecular weight protein contaminants, and low molecular weight protein contaminants useful in the present invention are obtained by methods known in the art. Typically, protein inclusion bodies which have been produced by recombinant microorganisms are processed to remove lipids and cell debris. The resulting relatively pure inclusion bodies containing recombinant protein and contaminating proteins, particularly high molecular weight recombinant protein dimers, oligomers and aggregates, are solubilized in a strong denaturant or detergent such as guanidine hydrochloride, sodium dodecyl sulfate (SDS), Triton, and other strong denaturants or detergents.

The resulting protein solution is separated from any insoluble materials; and the strong denaturant or detergent is removed to produce a protein solution containing the recombinant protein refolded into its native bioactive configuration, high molecular weight protein contaminants, low molecular weight contaminating proteins and other non-protein contaminants. Such solutions typically contain from about 1-50 mg/ml total protein and from about 0.05-5 mg/ml recombinant protein.

The flocculants are added to this solution according to the present invention to precipitate the high molecular weight contaminating proteins.

The high molecular weight contaminating proteins that precipitate upon addition of the flocculants are removed from the solution by conventional means such as filtration, centrifugation, and the like. The resulting protein solution containing the recombinant protein, low molecular weight contaminating proteins and other non-protein contaminants, if any, is further processed, as needed, to remove low molecular weight contaminating proteins and other non-protein contaminants such as precipitating agents, solubilizing agents, oxidizing agents, reducing agents, and the like. Typically, such non-protein contaminants are removed by dialysis, chromatography, or other suitable means, whereas the low molecular weight contaminating proteins are separated from the protein by ion-exchange or other forms of chromatography.

The protein solution is further processed to produce a protein or protein composition suitable for its intended use, typically by lyophilization. These methods are well known in the art.

Flocculants useful in the present invention are selected from polymer compounds which (1) contain a pendant quaternary group to impart positive charge to the polymer (this polymer could be a homopolymer of quaternary compounds such as CATFLOC-DL or SUPERFLOC 340 or a copolymer of quaternary compounds and polyacrylamides such as HERCOFLOC 1137), (2) are soluble in water, (3) are stable in wide pH ranges (4-12), (4) are stable at 0°-60° C., and (5) have a molecular weight (MW) of from about 100,000 to 12 million. These flocculants can generally be divided into two groups which are preferable for the method of the present invention: one group having a molecular weight of from about 100,000-500,000, preferably from about 200,000-300,000, and one group having a molecular weight of from about 1-11 million, preferably from about 1-7 million.

The lower molecular weight flocculants are required in lower concentration to effectively remove the impurity proteins whereas the higher molecular weight flocculants are generally required in larger concentration for impurity removal. However, the higher molecular weight flocculants are not only selective precipitant but surprisingly yield a precipitate that is very easy to separate from the solution. The precipitate formed using the higher molecular weight flocculants coagulates to form one big lump which can be scooped out easily from the solution. Examples of such flocculants are Hercules, HERCOFLOC 1137 and American Cyanamid's MAGNIFLOC 1596C.

Preferred compounds include NALCO 3DC052, NALCO 8853 and NALCO 8856 (obtainable from Nalco Chemicals, Naperville, Ill.); SUPERFLOC 340, MAGNIFLOC 1590C, MAGNIFLOC 1591C, MAGNIFLOC 1592C, MAGNIFLOC 1596C, MAGNIFLOC 1598C, MAGNIFLOC 1555C, MAGNIFLOC 1561C, MAGNIFLOC 1563C and MAGNIFLOC 581C (obtainable from American Cyanamid, Wayne, N.J.); HERCOFLOC 1137 (obtainable from Hercules, Wilmington, Del.); CATFLOC-DL, CATFLOC-T2 and CATFLOC-L (obtainable from Calgon Corp., Hinsdale, Ill.); and POLYHALL 347, POLYHALL 351 and POLYHALL 361 (obtainable from Celanese Corp., Jefferson Town, Ky.). SUPERFLOC® 315, 330, 340 are highly cationic, liquid, polyamine-type flocculants which are effective in solid-liquid separations in all types of mineral processing operations. The products in this series differ only in their molecular weights, SUPERFLOC 315 having the lowest molecular weight and SUPERFLOC 340 the highest. Typical properties for the flocculants are:

|  | SUPERFLOC Flocculants | | |
| --- | --- | --- | --- |
|  | 315 | 330 | 340 |
| Appearance | straw to amber-colored liquids | | |
| Specific gravity, 25° C. (77° F.) | 1.16 ± 0.02 | | |
| Viscosity, 25° C., cps | 175–350$^a$ | 550–750$^b$ | 4000–6000$^c$ |
| Effective viscosity$^d$, 25° C., cps | 250 | 500 | 4500 |
| pH | 5–7 | 5–7 | 4–5 |
| Solubility | infinitely soluble in water | | |
| Chemical reactivity | nonreactive | | |
| Shelf life | 12–24 months | | |
| Freezing point | 0° F. (−18° C.) | | |

$^a$Brookfield, #2 spindle @ 60 rpm
$^b$Brookfield, #2 spindle @ 30 rpm
$^c$Brookfield, #3 spindle @ 12 rpm
$^d$Viscosity at infinite shear speed SUPERFLOC 315, 330 and 340 flocculants are used in industry for thickening and dewatering mineral concentrates and tailings, either as primary flocculants, or in conjunction with a high molecular weight nonionic on anionic polyelectrolyte. They are considered especially effective in: (1) Coal refuse thickening and filtration, (2) Iron ore concentrate thickening and filtration, (3) Iron ore tailings thickening, (4) Sulfide mineral concentrate dewatering, and (5) Mine run-off water clarification.

MAGNIFLOC® 581C flocculant is a high molecular weight, liquid cationic flocculant. It is considered effective as a dewatering aid in the centrifugation, filtration and flotation of industrial and municipal waste sludges. It is also considered useful in other solid-liquid separations such as in secondary clarification, water clarification and oil demulsification. Properties for the flocculant are:

| Appearance | Amber liquid |
| --- | --- |
| Specific gravity @ 25° C. (88° F.) | 1.14–1.18 |
| Viscosity at 25° C. | 4000–6000 cps |
| pH | 4–6 |
| Solubility | Infinite in water |
| Chemical reactivity | Nonreactive |
| Shelf life, 50°–100° F. (10°–40° C.) | 12 to 24 months |
| Freezing point | 0° F. (−18° C.) |
| Flash point, closed cup | >200° F.(>93° C.) |

*Brookfield No. 3 spindle, 12 rpm

MAGNIFLOC 581C flocculant is a highly cationic polyelectrolyte which is especially effective in dewatering a wide range of industrial and municipal sludges. MAGNIFLOC 581C flocculant is recommended for liquid-solid separation processes such as: (1) gravity settling - improves floc formation yielding larger floc size and faster settling rates, (2) filtration - increases filtration rates and produces greater cake solids, (3) centrifugation - increases throughput while improving solids capture and centrate clarity, (4) air flotation - results in clearer underflows, greater throughput per square foot of surface and high solids float sludge, and (5) water clarification - for improved effluent quality, suspended solids and turbidity reduction.

NALCO® 3DC-052 is a high charge density moderate molecular weight aqueous cationic coagulant. Its general physical properties are:

| | |
|---|---|
| Form | Liquid |
| Color | Clear or Slight Amber |
| Odor | Slight |
| Charge in Solution | Cationic |
| Density (@ 60° F.) | 8.9 ± 0.1 lb/gal |
| Specific Gravity (@ 60° F.) | 1.07 ± 0.01 |
| Pour Point | 23° F. |
| Freeze Point | 18° F. |
| Freeze/Thaw Recovery | Complete |
| Flash Point (PMCC) | >200° F. |

NALCO 3DC-052 is considered an effective mineral processing flocculant to (1) improve recycle water quality by reducing solids carryover, (2) increase density and improve dewaterability of underflow solids, and (3) maximize solids capture in filtration.

Although the amount of flocculants needed to induce precipitation varies depending on protein concentration, protein characteristics, compound added, and the like, the flocculants typically are added to the solution in amounts sufficient to produce from about a 0.005-1% by volume solution of the compound, preferably from about a 0.01-0.5% solution by volume.

Among the preferred flocculants, SUPERFLOC 340 and HERCOFLOC 1137 appear to be the most effective in the present method. Both flocculants give nearly the same pST recovery of about 90% with a less than 0.2 P/M ratio. The required concentration of SUPERFLOC 340 (0.015 to 0.03%) to effect a good separation is much lower than that of the HERCOFLOC 1137 (0.15 to 0.25%) but the solid-liquid separation step is much easier with HERCOFLOC 1137.

Recombinant proteins recoverable using the method of the present invention can be any protein having a molecular weight greater than about 5000 daltons which are produced by recombinant microorganisms, typically in inclusion bodies. These include somatotropins, insulins, somatomedins, somatostatins, prolactins, placental lactogens, and the like.

Most preferably, recombinant somatotropins (molecular weight about 20,000) are recovered using the method of the present invention. The recombinant somatotropin can be a recombinant somatotropin from any species but are preferably bovine, porcine, avian, ovine, or human recombinant somatotropin, most preferably porcine or bovine recombinant somatotropin.

Methods for producing these recombinant proteins are well known in the art: For example, U.S. Pat. Nos. 4,604,359 and 4,332,717 disclose methods for producing human recombinant somatotropin; U.S. Pat. No. 4,431,739 discloses a method for producing recombinant somatotropins; E.P. Pat. Application 0 104 920 discloses a method for producing recombinant porcine somatotropin; U.S. Pat. No. 4,443,359 discloses a method for producing recombinant bovine somatotropin; Schoner, *Biotechnology*, 3(2):151-54, discloses a method for producing recombinant somatotropin, and Buell, *Nucleic Acid Res.*, 13, 1923-38 (1985) discloses a method for producing recombinant somatomedin C.

Also, European Patent Application Publication No. 0 103 395 describes the construction of a transformant strain of *E. coil* containing a first plasmid which codes for delta 9 (Ser) bovine somatotropin (somatotropin less its 9 N-terminal amino acids and having an additional serine residue at the N-terminus) under the control of the lambda P L promoter-operator and which has a Shine-Dalgarno region derived from bacteriophage mu. The transformant also contains a second plasmid, pcI857, which codes for the production of the pcI857 temperature-sensitive repressor protein. The repressor protein can be inactivated by raising the temperature to about 42° C., thereby inducing expression of delta 9 (Ser) bovine somatotropin. A transformant strain of this type, *E. coli* HB101 (P L-mu-delta 9 (Ser) bovine somatotropin and pcI857) has been deposited, with The American Type Culture Collection (ATCC), Rockville, Md. and assigned Accession No. 53030.

Construction of a similar transformant strain which codes for the production of delta 7 porcine somatotropin (porcine somatotropin less its first 7 N-terminal amino acids) is described in European Patent Application Publication No. 0 104 920. A transformant strain of this type, *E. coli* HB101 (P L-mu-delta 7 porcine somatotropin and pcI857) has been deposited with ATCC and assigned Accession No. 53031.

Strains 53030 and 53031 are prolific producers of delta 9 (Ser) bovine somatotropin and delta 7 porcine somatotropin, respectively. In both instances, the expressed protein is sequestered within the cell in the form of insoluble, biologically inactive inclusion bodies which are visible under a microscope. Other methods for many similar proteins are known in the art.

In the preferred embodiment, a recombinant somatotropin solution containing from about 1-50 mg/ml total protein and from about 0.05-5 mg/ml recombinant somatotropin is treated with from about 0.01-0.5% flocculant to precipitate the high molecular weight protein contaminants. The precipitate is removed by centrifugation and the recombinant somatotropin is recovered from the resulting solution using conventional means as described above.

Although the above recovery method is directed to recovering recombinant proteins, the method is equally applicable to separating and recovering non-recombinant proteins. For example, a solution containing a mixture of (1) a "useful or wanted protein", (2) high molecular weight proteins (molecular weight greater than about 1.5 times the molecular weight of the useful protein) and (3) low molecular weight proteins (molecular weight less than about 1.5 times the molecular weight of the useful protein) is treated according to the present invention to precipitate the high molecular weight proteins and thus separate the high molecular weight proteins from the useful protein and the low molecular weight proteins. The high molecular weight proteins are separated from the solution and discarded or further processed, as desired; the high molecular weight proteins can be recovered from the precipitate by redissolving the precipitate and recovering the proteins from the solution.

The useful protein is separated from the low molecular weight proteins by conventional means and further processed, if desired, to produce a protein product. The low molecular weight proteins which were separated from the useful protein are discarded or further processed, as desired. Typically, the low molecular weight proteins can be separated from the useful protein by chromatography or other means suitable for separating proteins having similar molecular weights. Many such protein separation means are well known to skilled artisans and are equally applicable in the present invention.

The invention having been generally described, the following examples are given as particular embodiments of the invention and to demonstrate the practice and advantages thereof. It is understood that the examples are given by way of illustration and are not intended to limit the specification or the claims to follow in any manner. In particular, inclusion bodies used in the experiments were prepared from transformed *E. coli* strains which produce delta-7 porcine somatotropin. The inclusion bodies were isolated from *E. coli* host strain HB101 transformed with a first plasmid (pL-mu-delta-7 pST) coding for delta-7 pST and a second plasmid (pcI857) coding for the temperature sensitive lambda phage repression protein. Many other strains of microorganisms produce inclusion bodies containing many types of recombinant proteins which will function in the present invention. Similarly, methods for growing these microorganisms to produce inclusion bodies are well known in the art.

EXAMPLE 1

Recombinant porcine somatotropin was recovered from microorganism inclusion bodies by (1) dissolving the inclusion bodies in sodium dodecyl sulfate (SDS), (2) removing insoluble contaminants from the solution to allow the rpST to refold into its bioactive configuration. The resulting protein solution contained the rpST, high molecular weight proteins and other non-protein contaminants.

A twenty-milliliter (ml) sample of the protein solution containing the rpST high molecular weight protein contaminants, low molecular weight contaminating proteins and other non-protein contaminants was added to 50 ml beaker which was placed in an ice-filled tub to keep the temperature between 5°–10° C.

A calculated volume of a 0.5% solution of SUPERFLOC 340 was added to the beaker to make the concentration of SUPERFLOC 340 equal to 0.0375 % by volume of the original feed. Reactants in the beaker were gently mixed using a Teflon coated stirring bar for about 1 to 3 minutes. Precipitates formed almost immediately. (Slower rate of addition of the precipitant gave a purer product with lower P/M ratio. Likewise, higher temperature, e.g., 25° C., yielded higher recovery. However, in actual practice, operation at higher temperature may not be feasible because of concerns regarding microbial growth.) Contents of the beaker were centrifuged and supernatant was filtered through a 0.2 micron filter to prepare the sample for gel permeation chromatography (GPC).

FIG. 1 shows the chromatogram for the feed and the product from which high molecular weight impurities have been removed by precipitation. Peaks in the GPC chromatogram (FIG. 1) obtained by passing the sample through Pharmacia's Superose 12 FPLC column characterize proteins of different molecular weights. For example, the peak appearing after 27.5 minutes corresponds to pST. Peaks appearing before the pST peak correspond to higher molecular weight proteins, some of which are polymers of pST. Numbers in the parentheses to the left of the chromatogram represent the pST concentration in parts per million and the polymer pST or high molecular weight impurities to monomer pST ratio. This ratio, called the P/M ratio, is used as a measure of the purity of the sample. The smaller the P/M ratio, the purer the sample.

FIG. 1 shows that when a feed containing 606 ppm of pST and a P/M ratio of 3.9 is treated with SUPERFLOC 340, a highly purified product with only <0.1 P/M ratio and 87.5% pST recovery is obtained.

EXAMPLE 2

Using the procedure described in Example 1, flocculants listed in Table 1 were tested. All selectively precipitated the poymeric pST or the high molecular weight impurities. Cationic flocculants containing quaternary ammonium groups are the most effective flocculants. The commercial flocculants obtained from American Cyanamid (SUPERFLOC 340), Calgon (CATFLOC-DL), and Hercules (HERCOFLOC 1137) are very effective in the present process. Many of the flocculants have a molecular weight of from about 200,000 to 300,000. However, some cationic flocculants with molecular weight in excess of 5-6 million daltons are not only selective precipitants but surprisingly yield a precipitate that is very easy to separate from the solution. In these cases, the whole precipitate coagulates to form one big lump which can be easily scooped out from the solution. Examples of such cationic flocculants which are polyacrylamide copolymers are Hercules, HERCOFLOC 1137 and American Cyanamid's MAGNIFLOC 1596C.

In terms of pST recovery and P/M ratio (Table 2), SUPERFLOC 340 and HERCOFLOC 1137 appear to perform similarly. The advantage of SUPERFLOC 340 over HERCOFLOC 1137 is that SUPERFLOC is required in much lower concentration. However, the floc characteristics of HERCOFLOC-precipitated pST polymer are superior, making the downstream processing simpler. CATFLOC-DL, which is a polymer of dimethyl diallyl ammonium chloride, performs like SUPERFLOC. However, because of its nontoxic nature and the absence of any hazardous ingredients according to OSHA Hazard Communication Standard (29 CFR 1910.1200), CATFLOC-DL may be a preferred flocculant.

Overnight storage of the centrifuged supernatant did not show any precipitation, indicating that the reaction was complete. The supernatant was analyzed using GPC and the data were then used to calculate the pST recovery and the P/M ratio in the supernatant product. The results are shown in Table 2.

Referring to Table 2, the results indicate that pST recoveries of about 90% with almost zero P/M ratio are obtained with optimum dose of the flocculant.

pST supernatant obtained after the flocculant precipitation was analyzed by Isoelectric Focusing (IEF). The results showed no difference among the flocculants and were similar to those obtained with a standard pST sample. This shows that, even after flocculant treatment, pST is essentially unchanged and is bioactive as native pST.

EXAMPLE 3

Using the procedure described in Example 1, flocculants SUPERFLOC 340, MAGNIFLOC 581C, HERCOFLOC 1137 and CATFLOC-DL were tested at different concentrations using several pilot-plant samples which had not been subjected to membrane purification. Each of the above reagents resulted in protein precipitation. However, the dosage to achieve certain purity level at high pST yield varied. This is due to batch-to-batch variations and due to variations in the efficiency of various flocculants to cause precipitation. Results of these tests are shown in Table 3 which summarizes the pST recovery and P/M ratio data for tested flocculants. These results indicate that there is a trade off between pST recovery and P/M ratio. The higher the flocculant dosage, the lower are the pST recovery and P/M ratio (lower P/M ratio means higher purity). In general, it is possible to do simple dose titrations as above to determine the optimum dose for a given flocculant such that desired purity is achieved with high recovery of pST. Obviously many modifications and variations of the present invention are possible in the light of the above teachings. It is therefore to be understood that within the scope of the appended claims the invention may be practiced otherwise than specifically described.

TABLE 1

List of Flocculants[1] Tested for Selective Precipitation of pST Polymer

| Reagent | Supplier |
|---|---|
| NALCO ® 3DC052, 8853, 8856 | Nalco Chemicals, Naperville, IL |
| SUPERFLOC ® 340 | American Cyanamid, Wayne, NJ |
| MAGNIFLOC ® 1590C, 1591C, 1592C, 1596C, 1598C 1555C, 1561C, 1563C | American Cyanamid, Wayne, NJ |
| HERCOFLOC 1137 | Hercules, Wilmington, DE |
| CATFLOC-DL, CATFLOC-T2 CATFLOC-L | Calgon Corp., Hinsdale, IL |
| CALGON 259, 289 | Calgon Corp., Hinsdale, IL |
| POLYHALL 347, 361 | Celanese Corp., Jefferson Town, KY |

[1] All are commercial products

TABLE 2

Comparison of the Precipitation and the Pilot-Plant Processes for the Prepurification of Porcine Somatotroin

| Feed | Wt % Recovery | P/M Ratio |
|---|---|---|
| SUPERFLOC 340 | | |
| BATCH 270 | 90 | 0.2 |
| BATCH 271 | 95 | <0.2 |
| BATCH 273 | 86 | 0.2 |
| BATCH 280 | 85 | 0.1 |
| BATCH 285 | >95 | <0.1 |
| BATCH 287 | 85 | 0.3 |
| BATCH 268-00E | 90 | 0.2 |
| AVERAGE | 89 | <0.2 |
| HERCOFLOC 1137 | | |
| BATCH 273 | 84 | <0.2 |
| BATCH 287 | 89 | 0.5 |
| BATCH 268-OOE | 94 | 0.3 |
| AVERAGE | 89 | 0.3 |
| CATFLOC-DL | | |
| BATCH 285 | 96 | <0.1 |
| NALCO 8853 | | |
| BATCH 280 | 84 | 0.2 |
| PILOT-PLANT PROCESS | | |
| AVERAGE | 75 | 0.4 |

TABLE 3 pST Recovery and P/M Ratio as a Function of Flocculant Dosage

| Flocculant Dose (Volume %) | Wt. % Recovery | P/M Ratio |
|---|---|---|
| SUPERFLOC 34 | | |
| 0.01875 | 90.0 | 0.32 |
| 0.0281 | 87.0 | 0.06 |
| 0.031 | 84.7 | 0.00 |
| MAGNIFLOC 581C | | |
| 0.0375 | 100.0 | 0.23 |
| 0.05 | 98.8 | 0.04 |
| 0.075 | 93.7 | 0.00 |
| HERCOFLOC 1137 | | |
| 0.10 | 89.9 | 1.3 |
| 0.15 | 84.4 | 0.15 |
| 0.175 | 78.0 | 0.00 |
| CATFLOC-DL | | |
| 0.0093 | 92.7 | 0.71 |
| 0.0125 | 89.3 | 0.17 |
| 0.01875 | 71.6 | 0.00 |

What is claimed is:

1. A method for recovering a recombinant somatotropin from a protein solution containing high molecular weight contaminating proteins, those proteins having a molecular weight greater than about 1.5 times the molecular weight of the recombinant somatotropin, and the recombinant somatotropin, comprising:
   directly adding to the solution in amounts sufficient to selectively precipitate the high molecular weight contaminating proteins a flocculant with (a) contains a pendant quaternary ammonium group to impart positive charge to the flocculant, (b) is soluble in water, (c) is stable from about pH 4–12, (d) is stable at from about 0°–60° C., and (e) is a polymer having a molecular weight of from about 100,000 to 12 million daltons;
   separating the precipitate from the solution; and
   recovering the recombinant somatotropin from the solution.

2. The method of claim 1 wherein the total protein concentration of the solution is from about 1–50 mg/ml and the recombinant protein concentration of the solution is from about 0.05–5 mg/ml.

3. The method of claim 1 wherein the flocculant is added directly to the solution in amounts sufficient to produce a 0.005–1% solution by volume.

4. The method of claim 1 wherein the flocculant has a molecular weight of from about 100,000–500,000.

5. The method of claim 1 wherein the flocculant has a molecular weight of from about 2–11 million.

6. The method of claim 1 wherein the high molecular weight contaminating proteins have a molecular weight of greater than about 30,000 and the protein to be recovered has a molecular weight of about 20,000.

7. The method of claim 1 wherein the recombinant somatotropin is bovine, porcine, avian, ovine or human recombinant somatotropin.

8. The method of claim 7 wherein the recombinant somatotropin is porcine or bovine recombinant somatotropin.

9. A method for separating and recovering a somatotropin from a protein solution containing the somatotropin, high molecular weight proteins, those proteins having a molecular weight greater than about 1.5 times the molecular weight of the somatotropin, and low molecular weight proteins, those proteins having a molecular weight less than about 1.5 times the molecular weight of the somatotropin, comprising:
   directly adding to the solution in amounts sufficient to selectively precipitate the high molecular weight contaminating proteins a flocculant with (a) contains a pendant quaternary ammonium group to impart positive charge to the flocculant, (b) is soluble in water, (c) is stable from about pH 4–12, (d) is stable at from about 0°–60° C., and (e) is a polymer having a molecular weight of from about 100,000 to 12 million daltons;

separating the precipitate from the solution; and recovering the somatotropin from the solution.

10. The method of claim 9 wherein the total protein concentration of the solution is from about 1–50 mg/ml and the protein concentration of the solution is from about 0.05–5 mg/ml.

11. The method of claim 9 wherein the flocculant is added directly to the solution in amounts sufficient to produce a 0.005–1% solution by volume.

12. The method of claim 9 wherein the flocculant has a molecular weight of from about 100,000–500,000.

13. The method of claim 9 wherein the flocculant has a molecular weight of from about 2–11 million.

14. The method of claim 9 wherein the high molecular weight contaminating proteins have a molecular weight of greater than about 30,000 and the protein to be recovered has a molecular weight of about 20,000.

* * * * *